United States Patent [19]

Klausz

[11] Patent Number: 5,111,492
[45] Date of Patent: May 5, 1992

[54] X-RAY DIAGNOSIS SYSTEM FOR ANGIOGRAPHIC EXAMINATION WITH DEVICE FOR THE AUTOMATIC TRACKING OF A CONTRAST MEDIUM

[75] Inventor: Remy Klausz, Neuilly S/Seine, France

[73] Assignee: General Electric CGR S.A., Issy les Molineaux, France

[21] Appl. No.: 724,170

[22] Filed: Jul. 1, 1991

[30] Foreign Application Priority Data

Jul. 6, 1990 [FR] France ................................ 90 08624

[51] Int. Cl.⁵ ............................................ H05G 1/64
[52] U.S. Cl. ........................................ 378/99; 358/111
[58] Field of Search ............................ 378/99; 358/111

[56] References Cited

U.S. PATENT DOCUMENTS

| | | | |
|---|---|---|---|
| 4,185,198 | 1/1980 | Fujimoto | 378/99 |
| 4,477,923 | 10/1984 | Baumann | 378/99 |
| 4,626,908 | 12/1986 | Tani | 378/99 |
| 4,723,261 | 2/1988 | Janssen | 378/99 |
| 4,941,169 | 7/1990 | Kawai | 378/99 |

FOREIGN PATENT DOCUMENTS

0146991 7/1985 European Pat. Off.
0374328 6/1990 European Pat. Off.

*Primary Examiner*—Craig E. Church
*Attorney, Agent, or Firm*—Walter C. Farley

[57] ABSTRACT

In a system of X-ray diagnosis for angiographic examinations, the passage of a contrast medium is detected by its physiological effects such as the rise in the temperature of the cutaneous tissues, by means of thermocouples positioned on the patient's body. The signals from the thermocouples are processed in a device which gives forward motion signals for a panel supporting the patient and signals for triggering the shooting in such a way that the radiological image includes an image of the contrast medium.

13 Claims, 3 Drawing Sheets

X-RAY DIAGNOSIS SYSTEM FOR ANGIOGRAPHIC EXAMINATION WITH DEVICE FOR THE AUTOMATIC TRACKING OF A CONTRAST MEDIUM

BACKGROUND OF THE INVENTION

1. Field of the Invention

The invention relates to systems of X-ray diagnosis and, more particularly, to systems used for the angiographic examination of the lower limbs. It also relates, in such systems, to a device that enables the tracking of the movement of a contrast medium or embolus and the taking of radiographic pictures in synchronism with said movement.

Angiography is the technique of X-ray diagnosis applied and adapted to the vascular system: namely the arteries, veins and perfused tissues. It makes use of iodine-based liquids, known as contrast liquids, that are opaque to X-rays. These liquids are injected into the vascular system in order to enable its display by differentiation with respect to the surrounding tissues. More precisely, the patient is stretched out on a table that is designed, for example, so as to move under a source of X-radiation associated with a receiver positioned on the other side of the patient from the source. In other systems of X-ray diagnosis, the table is fixed while the assembly consisting of the radiation source and receiver is movable. The practitioner injects a dose of contrast medium into an artery or vein of the patient stretched out on the table. Then, some seconds after this injection, he takes several successive radiographic shots of the patient so as to display the blood vessels and measure the progress in time of the dose of contrast medium, also called an embolus, in said blood vessels.

When the angiographic examination is limited to a part of the body that corresponds to the field of the receiver, namely to the dimensions of the radiographic film or of the radiological image intensifier, the pictures are made without moving the patient, namely the table, in relation to the source/receiver assembly or vice versa.

For angiographic examinations that concern the lower limbs, namely a length of about 120 centimeters, there are three methods used at present.

A first method consists in the use of a radiographic film of great length so as to cover the totality of the lower limbs in a single shot and take several successive shots, for example six of them, separated by time intervals that enable the progress of the contrast medium to be recorded. For each shot, the entire surface of the lower limbs is irradiated, thus leading to high exposure to X-rays. This is detrimental to the patient and entails a relatively high cost due to the price of large-format radiographic films. Furthermore, the number of shots available in the devices generally used is limited, usually to six. This means that the taking of the shots has to be spaced out in anticipating the progress of the contrast medium as efficiently as possible. Finally, an unnecessarily large part of the patient is irradiated since several images are made before or after the contrast medium reaches each point. This means that the time of passage of the contrast medium has to be lengthened and hence that, in order to preserve the same concentration, the volume injected has to be increased. This may be harmful to the patient, owing to the toxicity of the product, and may increase the cost of the examination.

A second method consists in examining the lower limbs zone by zone, each zone corresponding, for example, to a useful field of 35 cm × 35 cm or to a diameter of 30 or 35 cm. To this end, a first injection of contrast medium is made, and several successive shots are taken of the zone close to the injection. Then, the table or the source/receiver assembly is shifted to center the images on a neighboring zone. The same operations, namely the injection of the contrast medium and the recording of the images, can then be started again. The process is then recommenced in its entirety for the following zones. Thus, each series of shots of a zone makes it possible to see the passage of the contrast medium in the circulatory system of said zone from start to finish. Such a method leads to the carrying out several injections (in practice, as many injections as there are positions and radiographed zones): this takes time, results in considerable discomfort for the patient, and is costly in terms of contrast medium. Finally, this method leads to a great number of exposures and the result thereof is an additional irradiation of the patient and an increase in the cost of the examination when the receiver is constituted by a radiographic film.

A third method consists in carrying out a single injection of the contrast medium and in making a relative shift between the patient and the source/receiver assembly so that the part of the patient facing the source/receiver assembly is constantly the part where the concentration of contrast medium in the circulatory system enables the making of the desired images of this product. This third method calls for optimum synchronization, for the shifting operations, between the successive positions of the shots and the passage of the contrast medium. At present, the radiology tables designed for this type of examination have a selection of forward motions in fixed steps and at constant time intervals, the duration of which is left to the practitioner's discretion. They do not provide the practitioner with easy control over the examination stages which would enable him to follow the progress of the contrast medium irrespectively of the field of the receiver, the morphology of the patient and the pathological aspects of the case.

The foregoing description of the three methods of angiographic examination shows that the problem of determining the progress of the contrast medium along the circulatory system of the lower limbs is common to all three of them, even if the consequences are critical in varying degrees depending on the method considered.

A known way of following the passage of the contrast medium is for practitioners to use the patient's reactions and/or sensations during the passage of the contrast medium, for example sensations of heat, discomfort or pain, so that the taking of the different shots is matched in real time with the progress of the contrast medium.

An object of the present invention, therefore, is to make a device for the detection of the progress of the contrast medium that requires neither the patient's cooperation nor the same degree of attention on the practitioner's part.

Another object of the present invention is also the making of a system of X-ray diagnosis for angiographic examinations, that includes a device such as this to detect the progress of the contrast medium so as to synchronize the taking of the different shots with the position of the contrast medium detected by said device.

The invention is based on the observation that the contrast medium, through its composition in organic salts tri-substituted by iodine atoms, prompts reversible physiological modifications related to the concentration of contrast medium in the blood at the place concerned. The effect of the contrast medium may be expressed briefly and schematically, with respect to the invention, by the notion of vasodilatation of the blood vessels. This vasodilatation occurs in such a way that the result thereof is an in increase in the peripheral circulation of blood through the expansion of the small vessels. This phenomenon is propagated as and when the contrast medium moves on. It is this property that shall be turned to advantage in the contrast medium detection devices according to the present invention.

SUMMARY OF THE INVENTION

The invention relates to a system of X-ray diagnosis for the angiographic examination of a patient that includes a stand supporting an X-radiation source and a radiological image receiver cooperating with the source, a radiology table of the type including a panel mounted on a base, means to obtain relative shifts of the stand and of the panel, a device for the injection of a contrast medium into the patient's circulatory system and a device for the acquisition of the images detected by the receiver so as to finally obtain a radiological image of a patient's body, wherein said system further comprises means to detect the progress of the contrast medium in the patient's circulatory system and means to trigger, firstly, the relative shifting of the stand and of the panel in several positions and, secondly, the taking of the radiological image for these relative positions so that the radiological image obtained at each of these relative positions is recorded at an instant when the blood vessels of the zone, an image of which is recorded, show a significant concentration in contrast medium.

The means used to detect the progress of the contrast medium are sensors that are sensitive to the physiological effects induced by the contrast medium, such as the rise in the temperature of the cutaneous tissues or the increase in the volume of blood in the peripheral layers and hence in their water content.

In the case of a rise in temperature, the sensors are, for example, thermocouples positioned on the patient's body or are constituted by a thermographic camera positioned at a distance from the patient.

In the case of an increase in the volume of water to be detected, the sensors may be of the nuclear magnetic resonance type, of the type sensitive to variations of resistivity in low-frequency ac or dc current or, again, to impedance variations for electrical fields modulated at very high frequency.

It is also possible to use a radioactive contrast medium and to detect its progress by an appropriate detector such as a series of ionizing radiation detectors or a gamma camera.

BRIEF DESCRIPTION OF THE DRAWINGS

Other objects, features and advantages of the present invention shall appear from the following description of exemplary embodiments, said description being made with reference to the appended drawings, of which.

DETAILED DESCRIPTION OF THE INVENTION

Figure 1:
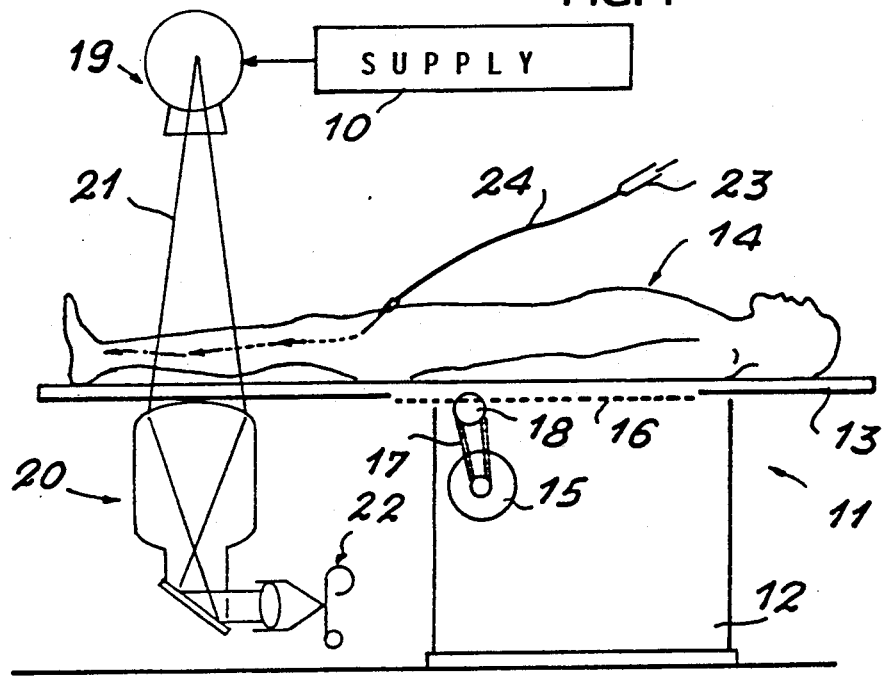
FIG. 1 shows a schematic view of a X-ray diagnostic system for an angiographic examination according to the prior art.

In FIG. 1, a prior art system of X-ray diagnosis for angiographic examinations has a radiology table and an assembly, called a stand, comprising an X-radiation source 19 and a receiver 20 of radiological images. The X-radiation source is powered by a standard type of electrical supply device 10.

The table 11 has a base 12 and a panel 13 to support a patient 14. The base 12 has means for the longitudinal shifting of the panel 13 that take the form of a motor 15 associated with a toothed rack 16 by means of a belt 17 and a toothed wheel 18.

The assembly formed by the source 19 and the receiver 20 is borne by means (not shown) that may consist of an arch in the form of a semi-arc of a circle, for example, one end of which bears the source while the other end bears the receiver. The arch itself is borne by a hinged arm, the motions of which enable the shifting if the source/receiver assembly with respect to the table 11.

In the position shown in FIG. 1, the source 19 emits an X-ray beam 21 that covers the legs of the patient 14. The X-radiation, which is attenuated by the legs, is detected by the receiver 20 which, in this case for example, is a luminance amplifier associated with a photographic camera 22.

It can be seen that, by shifting the panel 13 in relation to the source/receiver assembly, it is possible to obtain shots of the different parts of the patient's lower limbs.

The contrast medium is contained in a syringe 23 and is injected into the patient's femoral artery. For an angiographic examination of the lower limbs, this product is injected by means of a catheter 24.

At the outset, the practitioner positions the panel 13 to bring the source/receiver assembly to the level of the abdomen. At the instant of the injection, he takes several shots. He then shifts the assembly towards the legs by a length determined by the field of the receiver and again takes several shots, and so on until the position of the feet is reached. In this procedure, it is the practitioner's experience that enables him, firstly, to determine the instants at which the shots have to be taken and, secondly, to shift the panel 13 to the next position.

In the French patent application No. 88 17523 filed by the applicant on Dec.30, 1988 and entitled "RADIOLOGY SYSTEM FOR ANGIOGRAPHIC EXAMINATION AND METHOD OF IMPLEMENTATION", the angiographic examination proper is preceded by a radioscopy phase so as to determine and record different positions of the panel 13 as a function of the patient's anatomy. During the real examination, the table resumes the same positions automatically at instants determined on an a priori basis by the practitioner.

The present invention propose to detect the passage of the contrast medium so as to automatically achieve the taking of shots and the relative shifting of the patient and of the source/receiver assembly to follow the progress of the contrast medium.

To detect the passage of the contrast medium, the invention proposes the use of sensors that detect certain physiological modifications due to the contrast medium, notably the vasodilatation of the blood vessels.

Figure 4:
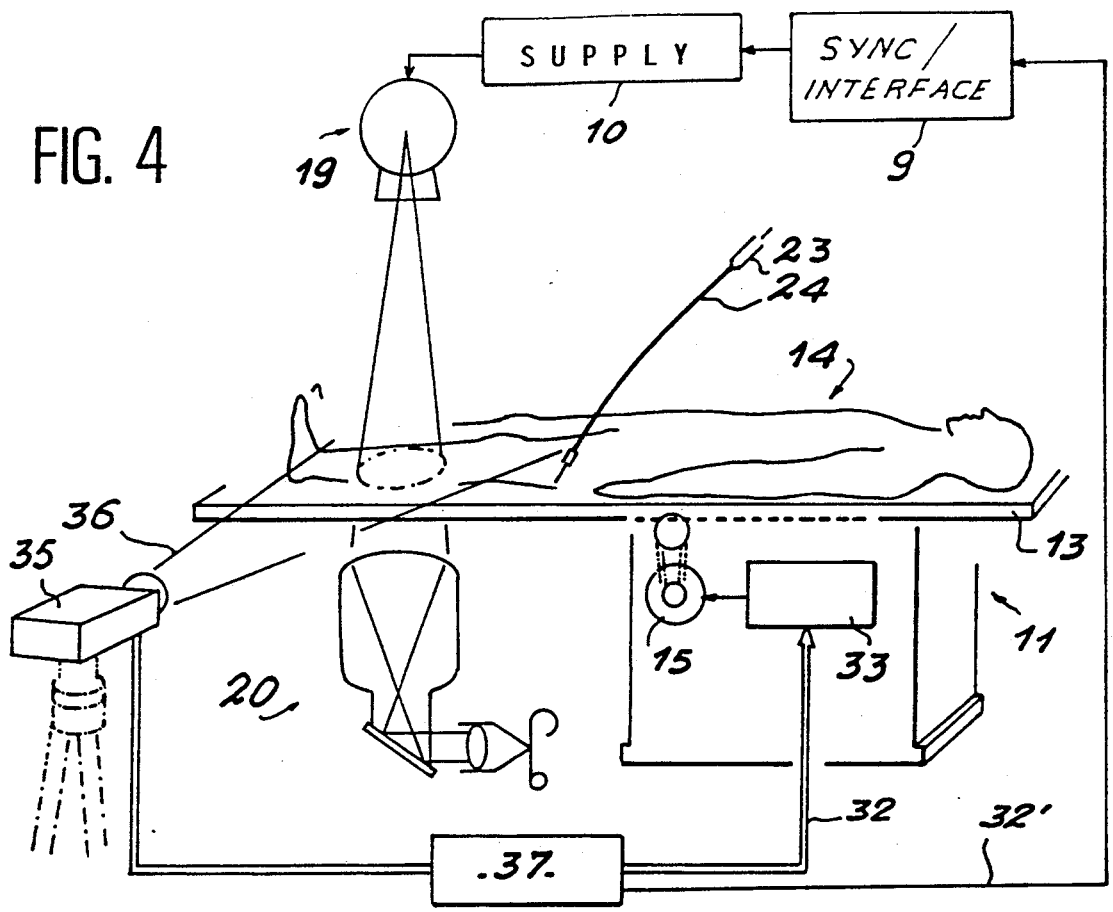
FIG. 4 shows a schematic view of a X-ray diagnostic system for angiographic examination, including a first device, according to the present invention, for the automatic tracking of a contrast medium.
Figure 5:
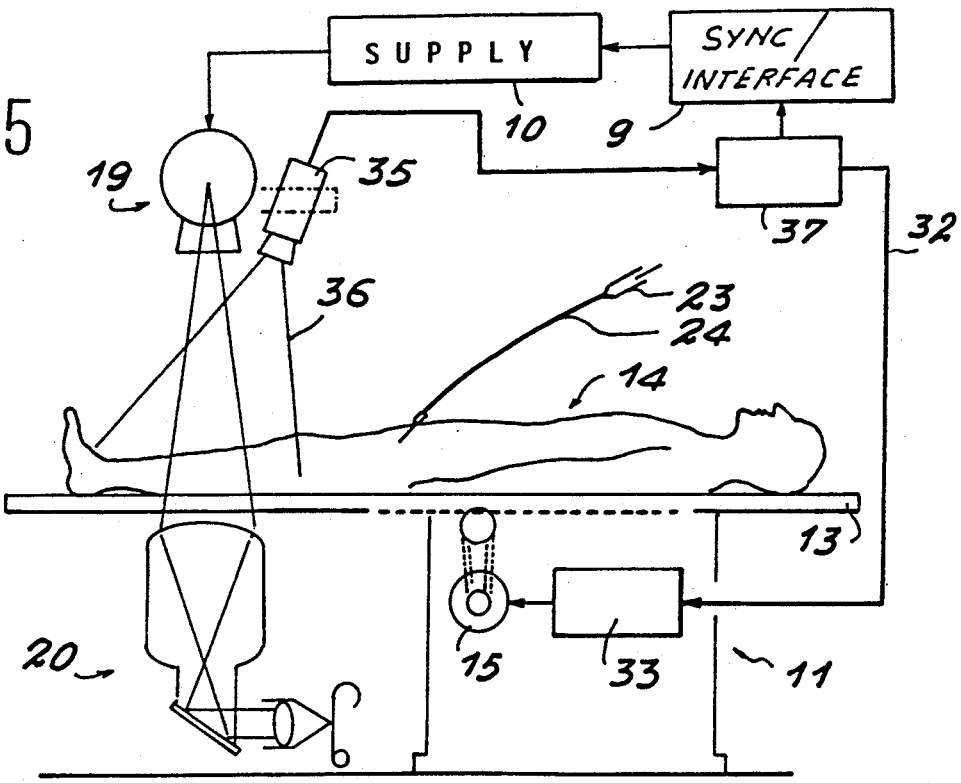
FIG. 5 shows a schematic view of a variant of the X-ray diagnostic system for angiographic examination, as described with reference to FIG. 4.

This vasodilatation notably has the effect of increasing the peripheral blood circulation by the expansion of the small vessels, and the result thereof is an increase in the patient's skin temperature. The invention proposes to detect this cutaneous temperature by sensors positioned on at least one of the lower limbs: this is the device that shall be described with reference to FIGS. 2 and 3. The invention also proposes the detection of this rise in temperature by means of a telethermographic camera positioned on a lateral side of patient (FIG. 4) or above the patient in association with the X-radiation source 19 (FIG. 5).

The vasodilatation also prompts an increase in the volume of blood in the peripheral layers of the tissues and hence in their water content. The invention therefore proposes the use of detectors that are sensitive to the water content. This is the case with nuclear magnetic resonance instruments that enable the measurement of the density of protons and, hence, of water. This is also the case with instruments that measure variations of resistivity in low-frequency ac or dc current. Finally there are instruments that measure impedance variations for electrical fields modulated at very high frequency.

As a rule, any detector that is sensitive to the passage of the contrast medium through the effects that it induces can be used in the invention.

To follow the progress of the contrast medium, the invention also proposes to make it radioactive and to detect the emission of gamma rays by a scintigraphic apparatus for example.

Two embodiments of a detector of the passage of an contrast medium shall now be described in greater detail with reference to FIGS. 3 to 6, the signals given by these detectors being used to determine firstly the position of the contrast medium and then, in a system of X-ray diagnosis for angiographic examinations, to change the relative positions of the patient and of the source/receiver assembly.

In the different FIGS. 1 to 5, identical elements are given the same references in order to make the description clearer.

Figure 2:
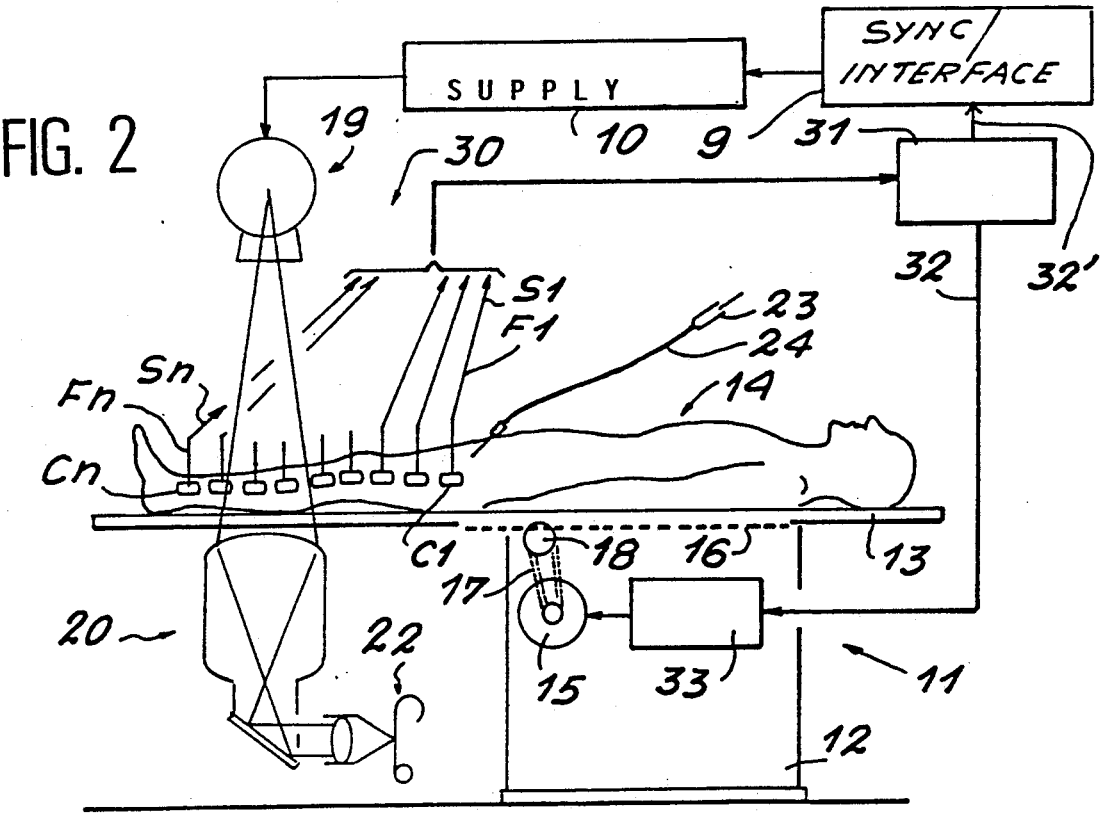
FIG. 2 shows a schematic view of a X-ray diagnostic system for angiographic examination, including a first device for the automatic tracking of a contrast medium according to the present invention.

The detection device 30 of the X-ray diagnostic system of FIG. 2 includes a series of n sensors $C_1$ to $C_n$ sensitive to the physical modifications induced by the physiological modifications that are prompted by the propagation of the contrast medium. The sensors $C_1$ to $C_n$ are positioned on one of the patient's legs or on both of them depending on whether one or both legs are to be radiographed. The sensors $C_1$ to $C_n$ respectively give electrical signals $S_1$ to $S_n$ which are applied to a processing device 31 by means of conductors $F_1$ to $F_n$. The processing device 31 gives signals on a conductor 32. These signals control the shifting of the panel 13 through a control circuit 33 for the control of the motor 15. Furthermore, the devices 31 gives signals on a conductor 32'. These signals, through the synchronization and interface device 9 and the supply device 10, control the source 19 to make it emit X-rays at determined instants so as to obtain a radiological image.

Figure 3:
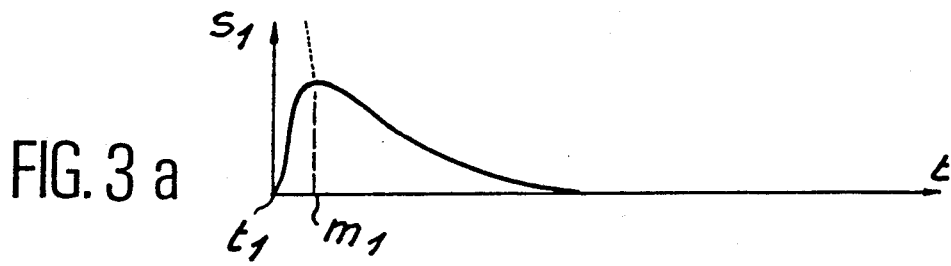
FIGS. 3a to 3e are graphs showing the shape of the signals detected by the sensors used in the first device of FIG. 2 for the automatic tracking of a contrast medium.
Figure 3:
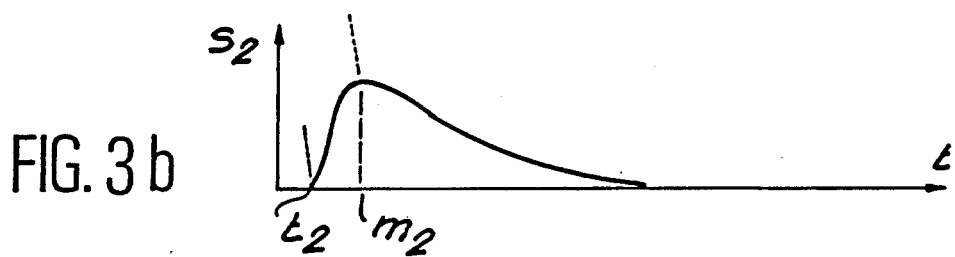
Figure 3:
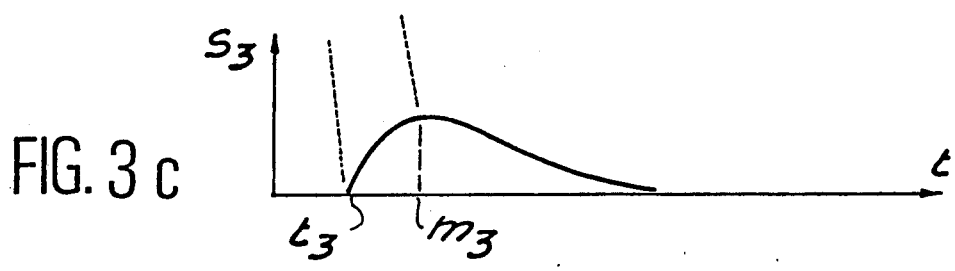
Figure 3:
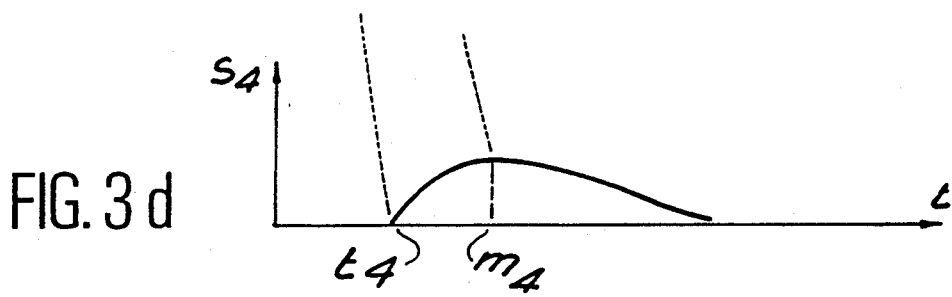
Figure 3:
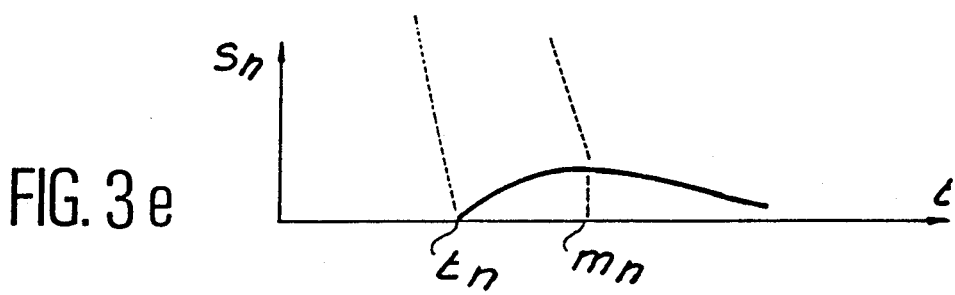

FIGS. 3-a to 3-e are graphs of the amplitudes of the signals $S_1$, $S_2$, $S_3$, $S_4$ and $S_n$ as a function of the time t, the starting point corresponding to the instant of injection of the contrast medium. The signals $S_1$ to $S_n$ are similar to one another but are time-lagged, i.e. delayed with respect to one another owing to the fact that they correspond to sensors located at distances $d_1$, $d_2$, $d_3$, $d_4$...$d_n$ that are increasingly away from the point of injection of the contrast medium. The shape of each signal is such that it appears at an instant $t_1$, $t_2$, $T_3$, $t_4$ or tn, increases relatively swiftly up to a maximum value at the instants $m_1$, $m_2$, $m_3$, $m_4$...$m_n$ and then decreases relatively slowly. As a result of the dilution of the contrast medium, as and when it moves, its physiological effects are increasingly less accentuated so that the signals $S_1$ to $S_n$ get increasingly wider, i.e. the slopes on either side of the maximum value are increasingly smaller when the index n increases.

As indicated here above, the processing of the signals $S_1$ to $S_n$ is done by the device 31 so as to determine the real position of the contrast medium and the instant of forward motion of the panel 13 so that each shot can include an image of the contrast medium. To this effect, the processing program takes account of the delay between the instant when the contrast medium passes to the position of a sensor $C_2$, for example, and the instant $t_2$ of the appearance of the start of the signal $S_2$ or $m_2$ of its maximum value. To carry out this program, a model of propagation of the contrast medium will be set up by a statistical study of a large number of cases.

The sensors that can be used are of several types, depending on the physiological effects that they may be led to detect.

Thus, if the rise in the skin temperature is put to use, the sensors are of the thermometrical type, for example thermocouples. This is the embodiment of FIG. 2.

It is also possible to make profitable use of the variations of resistivity in low-frequency dc or ac current. Besides, these variations can be used to make so-called electrical tomography images. A method such as this is described, for example, in the article "ELECTRICAL IMPEDANCE TOMOGRAPHY—APPLIED POTENTIAL TOMOGRAPHY" in the journal Clinical Physics And Physiological Measurement, vol. 8 and 9, 1988, published by The Institute of Physical Sciences in Medicine. The arrangement of the sensors will be optimized, either to indicate the total water content in a section of the legs or to indicate the water content in the peripheral layers of the legs. This method is particularly efficient, inasmuch as the parameter measured is sensitive both to the temperature and to the water content of the tissues.

Instead of sensors placed directly on the patient's legs, the invention proposes the use of one or more sensors that are positioned at a distance from the patient and are sensitive either to the rise in the cutaneous temperature or to the increase in the volume of blood in the peripheral layers of the tissues, and hence to the increase in their water content.

In the sensors of the first category, namely the sensors sensitive to the rise in temperature, the invention proposes the use of the thermographic camera 35 (FIG. 4), the beam 36 of which is aimed at all of the patient's lower limbs or at a limited zone located upline of the zone for which a radiological examination is made. The electrical signals in the form of images given by the camera 35 are processed in a processing device 37 which then gives, firstly, forward motion signals of the motor 15, via conductors 32 by means of the control device 33 identical to that of FIG. 2 and, secondly, signals to control the source 19, via conductors 32', a synchronization and interface device 9 and a power supply 10.

In the embodiment of FIG. 5, the camera 35 is positioned on a support placed on one side or the other of the table 11. This makes it bulky and hampers access to the patient. Thus, the invention proposes the fixing of the camera 35 to the X-ray tube 19 so that its field 36 contains the totality of the radiographed field increased by at least one zone equivalent to said radiographed field towards the patient's feet.

It is also possible to use sensors other than those described here above with reference to FIGS. 2 to 5.

It is thus possible to use a nuclear magnetic resonance apparatus that enables the direct measurement of the density of protons and hence of water. In an application such as this, the nuclear magnetic resonance instrument may be made in a rudimentary way, for it is not necessary to obtain a high quality image. Such an instrument may use low intensity magnetic fields that can be set up by resistive or permanent magnets.

It is also possible to use instruments that detect the impedance variations for electrical fields modulated at very high frequency in the microwave range. An instrument such as this is, for example, described in the thesis by Hugues de Talhouet, "CONTRIBUTION TO THE IMPROVEMENT OF RESOLUTION IN MONOCHROMATIC MICROWAVE IMAGING", presented on Dec. 19, 1986 at the University of Paris-South.

The sensors that have been described here above are designed to detect the physiological effects induced by the passage of the contrast medium, namely effects such as the rise in the temperature of the cutaneous tissues or the increase in the water content of the peripheral layers of the tissues.

Sensors that are not based on the detection of physiological effects may also be used, for example a radiology instrument of the X-ray type that detects the contrast medium by its greater opacity. It is also possible to use a specific type of contrast medium, modified to emit gamma rays, and to detect its passage by a scintigrapic apparatus known as a gamma camera.

What is claimed is:

1. A system of X-ray diagnosis for the angiographic examination of a patient, comprising a stand supporting an X-radiation source and a radiological image receiver cooperating with the source, a radiology table of the type including a panel mounted on a base, means to obtain relative shifts of the stand and of the panel, a device for the injection of a contrast medium into the patient's circulatory system and a device for the acquisition of the images detected by the receiver so as to finally obtain a radiological image of a patient's body, wherein said system further comprises means for detecting the progress of the contrast medium in the patient's circulatory system and means responsive to said means for detecting for triggering, firstly, the relative shifting of the stand and of the panel in several positions and, secondly, the taking of the radiological image for these relative positions so that the radiological image obtained at each of these relative positions is recorded at an instant when the blood vessels of the zone, an image of which is recorded, show a significant concentration in contrast medium.

2. A system of X-ray diagnosis according to claim 1, wherein means for detecting the progress of the contrast medium comprise sensors that are sensitive to the physiological effects induced by the contrast medium.

3. A system of X-ray diagnosis according to claim 1, wherein means for detecting the progress of the contrast medium are of the thermometrical type so as to detect the rise in the temperature of the cutaneous tissues.

4. A system of X-ray diagnosis according to claim 3, wherein means for detecting the progress of the contrast medium are thermocouples positioned on the patient's body.

5. A system of X-ray diagnosis according to claim 1, wherein means for detecting the progress of the contrast medium are constituted by a thermographic camera positioned at a distance from the patient.

6. A system of X-ray diagnosis according to claim 1, wherein means for detecting the progress of the contrast medium is a thermographic camera that is positioned on either one of the longitudinal sides of the radiology table.

7. A system of X-ray diagnosis according to claim 1, wherein means for detecting the progress of the contrast medium is a tomographic camera that is positioned above the radiology table and is associated with the X-ray tube.

8. A system of X-ray diagnosis according to claim 1, wherein means for detecting the progress of the contrast medium are of the type used to detect the variations of resistivity in low-frequency dc or ac current.

9. A system of X-ray diagnosis according to claim 1, wherein means for detecting the progress of the contrast medium are of the type used to detect the variations of impedance for electrical fields modulated at very high frequency.

10. A system of X-ray diagnosis according to claim 1, wherein means for detecting the progress of the contrast medium are of the nuclear magnetic resonance type so as to measure the variation of the density of water.

11. A system of X-ray diagnosis according to claim 1, wherein said contrast medium comprises a radioactive substance and wherein means for detecting the progress of the contrast medium are of the type used to detect gamma radiation.

12. A system of X-ray diagnosis according to claim 1, wherein said contrast medium comprises a radioactive substance and wherein means for detecting the progress of the contrast medium are constituted by a scintigraphic apparatus.

13. A system of X-ray diagnosis according to claim 1, wherein means for detecting the progress of the contrast medium are constituted by an X-radiation radiology apparatus that detects the contrast medium by its opacity to X-radiation.

* * * * *